(12) United States Patent
MacDonald et al.

(10) Patent No.: US 7,700,120 B2
(45) Date of Patent: Apr. 20, 2010

(54) **ADJUVANCY AND IMMUNE POTENTIATING PROPERTIES OF NATURAL PRODUCTS OF *ONCHOCERCA VOLVULUS***

(75) Inventors: Angus J. MacDonald, Southampton (GB); Sara Lustigman, New York, NY (US)

(73) Assignee: New York Blood Center, New York, NY (US)

( * ) Notice: Subject to any disclaimer, the term of this patent is extended or adjusted under 35 U.S.C. 154(b) by 681 days.

(21) Appl. No.: 11/153,222

(22) Filed: Jun. 15, 2005

(65) Prior Publication Data

US 2006/0039921 A1    Feb. 23, 2006

Related U.S. Application Data

(60) Provisional application No. 60/580,254, filed on Jun. 15, 2004.

(51) Int. Cl.
  *A61K 39/00* (2006.01)
  *A61K 45/00* (2006.01)
  *A61K 39/12* (2006.01)
  *A61K 39/38* (2006.01)
  *A61K 38/00* (2006.01)
  *C07K 14/00* (2006.01)

(52) U.S. Cl. ............... 424/265.1; 424/278.1; 424/191.1; 424/192.1; 424/204.1; 424/184.1; 514/2; 530/822; 530/820; 530/350

(58) Field of Classification Search ............... 424/265.1, 424/192.1, 193.1, 191.1, 184.1, 204.1, 278.1; 514/2; 530/350, 822, 820
See application file for complete search history.

(56) References Cited

U.S. PATENT DOCUMENTS

| | | | |
|---|---|---|---|
| 4,370,265 A | * | 1/1983 | Adam et al. .................. 536/53 |
| 5,169,840 A | | 12/1992 | Otterlei et al. ................. 514/55 |
| 6,537,552 B1 | | 3/2003 | Minion et al. ............. 424/190.1 |
| 6,572,866 B1 | | 6/2003 | Torcia ..................... 424/278.1 |
| 6,586,409 B1 | | 7/2003 | Wheeler ...................... 514/44 |
| 6,630,161 B1 | | 10/2003 | Leesman .................... 424/455 |
| 6,635,261 B2 | | 10/2003 | LaPosta et al. ............ 424/278.1 |
| 6,649,170 B1 | | 11/2003 | Lindblad et al. ......... 424/248.1 |
| 6,676,958 B2 | | 1/2004 | Gerber ....................... 424/434 |
| 6,682,746 B2 | | 1/2004 | Hennessy et al. ......... 424/278.1 |
| 6,713,068 B1 | | 3/2004 | Audonnet et al. ........ 424/206.1 |
| 6,723,322 B1 | | 4/2004 | Lustigman et al. ....... 424/191.1 |

FOREIGN PATENT DOCUMENTS

WO    WO 96/37218 A1 *    11/1996

OTHER PUBLICATIONS

MacDonald et al. Parasite Immunology 26: 53-62, Jan. 2004.*
Brady et al., *Infection and Immunity* 67(10):5372-5378 (1999).
Holland, et al., *Eur. J. Immunol.* 30:1977-1987 (2000).
McInnes et al., *J. Immunol.* 171(4):2127-33 (2003).
Okano et al., *J. Immunol*, 167:442-450 (2001).
Paterson et al., *Infection and Immunity* 70(11):6058-6067 (2002).
Tawe et al., *Molecular and Biochemical Parasitology* 109:91-99 (2000).
Turaga et al., *Infection and Immunity* 68(4):1905-1911 (2000).
Zarour et al., *Cancer Research* 62:213-218 (2002).
MacDonald, et al. "rOv-ASP, a recombinant secreted protein of the helminth *Onchocerca volvulus*, is a potent adjuvant for inducing antibodies to ovalbumin, HIV-1 polypeptide and SARS-CoV peptide antigens," Vaccine 2005, 23:3446-3452.

* cited by examiner

*Primary Examiner*—S. Devi
(74) *Attorney, Agent, or Firm*—Louis C. Cullman; Michelle S. Glasky; K&L Gates LLP

(57) ABSTRACT

The present invention relates to a method for potentiating a specific immune response to an antigen in a mammal in need thereof. The method comprises administering to the mammal an effective amount of Ov-ASP, or at least one subunit of Ov-ASP, and an antigenic moiety.

15 Claims, 7 Drawing Sheets

ADJUVANCY AND IMMUNE POTENTIATING PROPERTIES OF NATURAL PRODUCTS OF ONCHOCERCA VOLVULUS

This application claims benefit of U.S. Provisional Application No. 60/580,254, filed Jun. 15, 2004, incorporated herein by reference.

BACKGROUND OF THE INVENTION

The increased threat of a bioterrorist attack in recent years highlights the critical need for the development of potent vaccine formulations to protect the susceptible population. Vaccine formulations contain antigens that induce immunity against pathogenic agents. However, immune responses to many antigens, while detectable, are frequently of insufficient magnitude to afford protection against a disease process mediated by the agents expressing those antigens. In such situations, it is necessary to include an adjuvant along with the antigen in the vaccine formulation.

An adjuvant is a compound that, when used in combination with specific vaccine antigens, potentiates the resultant immune response. The mechanism of action of adjuvants is not precisely known, and may not be the same for all adjuvants. However, it is believed that adjuvants prolong the bioavailability of an antigen. Adjuvants also seem to increase the size of the antigen, thus increasing the likelihood of phagocytosis. Additionally, most adjuvants have a stimulatory effect on the cell-mediated branch of the immune system, i.e., on T lymphocytes (T cells).

There are two well-defined subpopulations of T cells: T cytotoxic (Tc) cells and T helper (Th) cells. T cytotoxic cells kill intracellular pathogens. On the other hand, Th cells exert most of their functions through secreted cytokines. T helper cells are further divided into Th1 and Th2 cell types. Differences in cytokine-secretion patterns of the Th cell types determine the type of immune response made to a particular antigen challenge.

In general, Th1 cells stimulate cytotoxic responses against intracellular viruses, bacteria and protozoa via secretion of interferon-gamma (IFN-$\gamma$) and other pro-inflammatory cytokines. The cytotoxic responses include the activation of Tc cells. In contrast, Th2 cells are induced by allergens and helminth parasites, and are characterized by the secretion of interleukins, e.g., IL-4, IL-5, etc. Both Th cell types stimulate the humoral branch of the immune system, i.e., the B lymphocytes.

Different pathogens elicit different types of cell-mediated immune responses. For example, infecting mice with a helminth parasite polarizes the immune response to Th2 activation. In some cases, the polarization is so potent that a Th1-dominant response to an infectious pathogen can be inhibited by the introduction of a helminth parasite. (Brady et al "*Fasciola hepatica* suppresses a protective Th1 response against *Bordetella pertussis*" *Infect. Immun.* 67: 5372-5378 (1999).) Similarly, a Th1-mediated mouse autoimmune disease can be ablated by introducing a helminth parasite into mice (Cooke et al. "Infection with *Schistosoma mansoni* prevents insulin dependent diabetes mellitus in non-obese diabetic mice" *Parasite Immunol.* 21:169-176 (1999)).

Additionally, the anti-inflammatory properties of the products of two helminth parasites have been shown to be capable of down-modulating inflammatory Th1 responses in mice. In particular, body fluid from the pig roundworm parasite, *Ascaris suum*, potently stimulates cytokines characteristic of Th2 cells. (Paterson et al., "Modulation of a Heterologous Immune Response by the Products of *Ascaris suum*" *Infect. Immuunol.* 70:6058-67 (2002)). Also, a secreted glycoprotein product, ES-62, of a rodent parasite has been found to have broad anti-inflammatory properties that inhibit Th1 cytokine production in experimentally-induced arthritis in mice (McInnes et al., "A Novel Therapeutic Approach Targeting Articular Inflammation Using the Filarial Nematode-Derived Phosphorylcholine-Containing Glycoprotein ES-62" *J. Immuunol.* 171:2127-33 (2003)). This product is currently being developed as a novel anti-inflammatory therapeutic.

Recently, two helminth products have been reported as acting as adjuvants. Both are strong inducers of Th2 responses to bystander proteins in a vaccine. In particular, proteins secreted by adult *Nippostrongylus brasiliensis* (a parasite of rodents) were found to be strong inducers of Th2 responses in mice immunized with an unrelated protein (Holland et al., "Proteins secreted by the parasitic nematode *Nippostrongylus brasiliensis* act as adjuvants for Th2 respones" *Eur. J. Immunol.* 30 (7):1977-1987 (2000)). Similarly, lacto-N-fucopentaose III, a carbohydrate found on the surface of the eggs of a human parasite, *Schistosoma mansoni*, acted as a Th2 adjuvant for a bystander protein when injected into mice (Okano et al., "Lacto-N-fucopentaose III Found on *Schistosoma mansoni* Egg Antigens Functions as Adjuvant for Proteins by Inducing Th2-Type Response" *J. Immunol.* 167:442-450 (2001)).

Until the present invention, products from helminths have been found to be potently Th2 dominant. Accordingly, their use as adjuvants has been to induce the Th2 cell type responses. Although Th2 cell type activation is important, Th1 cell type activation is critical for the efficacy of certain vaccines. In addition to providing a different cytokine profile than that provided by Th2 cells, Th1 cells activate cytotoxic effector mechanisms which Th2 cells do not activate.

Moreover, other adjuvants presently used in human vaccines also are not effective in stimulating cytotoxic responses to intracellular pathogens. These adjuvants include aluminum salts, e.g., aluminum potassium sulfate, aluminum phosphate and aluminum hydroxide. Without the ability to stimulate cytotoxic responses to intracellular pathogens, the use of such adjuvants is limited.

In additional to protecting against infectious diseases, vaccination is becoming significant in other developing technologies. These technologies include, for example, vaccination against syngeneic tumors. In such new approaches, it is important to be able to induce different types of immune responses.

Accordingly, there is a critical need for safe and effective adjuvants and therapeutics capable of boosting immune responses to a wide variety of pathogens and against tumors. There is a particular need for adjuvants that boost Th1 cell type responses.

SUMMARY OF THE INVENTION

In one embodiment, the present invention relates to a vaccine composition or immunogenic composition which comprises an antigenic moiety; and an adjuvant comprising an effective amount of Ov-ASP, or of at least one subunit of Ov-ASP. Ov-ASP includes Ov-ASP-1, Ov-ASP-2 and Ov-ASP-3.

In another embodiment, the present invention relates to a method for potentiating a specific immune response to an antigen in a mammal in need thereof. The method comprises administering to the mammal an effective amount of Ov-ASP, or at least one subunit of Ov-ASP; and an antigenic moiety.

In a further embodiment, the present invention relates to a method for stimulating a cellular response with cytokine secretion in a mammal in need thereof. The method comprises administering to the mammal an effective amount of Ov-ASP, or at least one subunit of these proteins, wherein the cytokine secretion is stimulated.

In an additional embodiment, the present invention relates to a method of generating an immune response or vaccinating a mammal in need thereof against onchocerciasis. The method comprises administering to the mammal an effective amount of Ov-ASP, or antigenic fragments of Ov-ASP, and a pharmaceutically-acceptable carrier.

In another aspect, the present invention relates to a method of preventing SARS in a mammal in need thereof. The method comprises administering to the mammal a vaccine composition comprising a SARS-CoV polyamino acid, and an effective amount of Ov-ASP, or at least one subunit of Ov-ASP. In another aspect, the present invention relates to a method of preventing HIV in a mammal in need thereof. The method comprises administering to the mammal a vaccine composition comprising an HIV-1 polyamino acid, and an effective amount of OV-ASP, or at least one subunit of Ov-ASP.

DETAILED DESCRIPTION OF THE INVENTION

Figure 1:
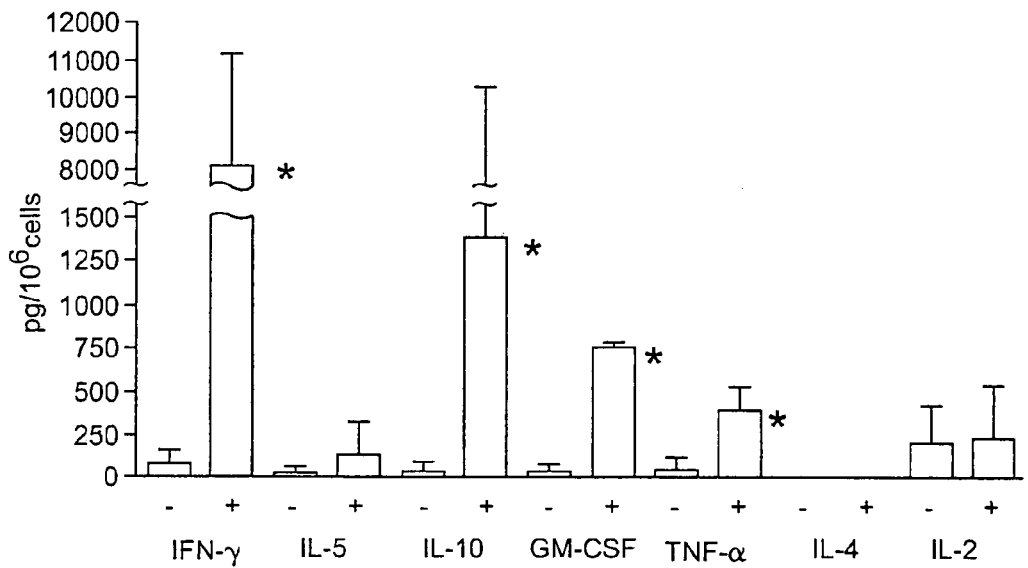
FIG. 1. Cytokine secretion induced by rOv-ASP-1 (5 μg/mL) from PBMC obtained from individuals (n=14) never exposed to *Onchocerca volvulus*. Cells were incubated with rOv-ASP-1 (+) or culture medium alone (−). *=P<0.05 versus cells in culture medium alone. Values are the mean±SD.

The present invention comprises pharmaceutical compositions and methods to stimulate, i.e., induce and/or potentiate, immune responses in mammals. The invention includes the unexpected discovery that proteins from a helminth parasite, *Onchocerca volvulus*, can stimulate various aspects of the mammalian immune response.

The proteins used in the pharmaceutical compositions and methods of the invention are members of the Ov-ASP (Onchocerca volvulus activation-associated secreted protein) family. Native Ov-ASPs are located in secretory granules of the glandular esophagus and the surface of the infective third stage larvae of the helminth Onchocerca volvulus.

Members of the Ov-ASP family include Ov-ASP-1, Ov-ASP-2 and Ov-ASP-3. The sequence of Ov-ASP-1 is shown in SEQ ID NO: 1. The sequence of Ov-ASP-2 is shown in SEQ ID NO:2. The sequence of Ov-ASP-3 is shown in SEQ ID NO:3. Ov-ASP used in the compositions and methods of the invention need not be 100% identical to SEQ ID NO:1, SEQ ID NO:2 or SEQ ID NO:3, as long as the protein retains the immune-stimulating properties of SEQ ID NO:1, SEQ ID NO:2 or SEQ ID NO:3. For example, Ov-ASP, for the purposes of this specification, is approximately 90%, 91%, 92%, 93%, 94%, 95%, 96%, 97%, 98%, 99% or 100% identical to SEQ ID NO:1, SEQ ID NO:2 or SEQ ID NO:3.

One or more subunits (i.e., fragments) of Ov-ASP can be used in the compositions and methods of this invention. A subunit can be any length which produces the desired stimulation of an immune response (i.e., an active subunit). The minimum number of amino acids of a subunit includes, for example, at least about twenty, thirty, forty, fifty, sixty, seventy, eighty, and ninety amino acids. The maximum number of amino acids of a subunit includes, for example, at most about two hundred fifty three, two hundred fifty, two hundred forty, two hundred thirty, two hundred twenty, two hundred ten, two hundred, one hundred ninety, one hundred eighty, one hundred seventy, one hundred sixty, one hundred fifty, one hundred forty, one hundred thirty, one hundred twenty, one hundred ten, and one hundred amino acids. A suitable range of amino acids includes any number from the minimum and any number from the maximum.

For the purposes of this specification, "Ov-ASP" includes a full length Ov-ASP-1, or one or more subunits of a full length Ov-ASP-1; a full length Ov-ASP-2, or one or more subunits of a full length Ov-ASP-2; or a full length Ov-ASP-3, or one or more subunits of a full length Ov-ASP-3.

Ov-ASP, and subunits of these proteins, can be prepared by methods known in the art. Preferably, the proteins are produced recombinantly. For example, recombinant protein, rOv-ASP-1, was expressed in *E. coli* using cDNA encoding Ov-ASP-1 (Ov-ASP-1: GenBank accession number AF020586). This recombinant protein has a molecular weight of 24,871 Da. Recombinant protein, rOv-ASP-2, was expressed in *E. coli* using cDNA encoding Ov-ASP-2 (Ov-ASP-2: GenBank accession number H39490). This recombinant protein has a molecular weight of 29,047 Da. Recombinant protein, rOv-ASP-3, was expressed in *E. coli* using cDNA encoding Ov-ASP-3 (Ov-ASP-3: GenBank accession number AA917267). This recombinant protein has a molecular weight of 24,744 Da. See Tawe et al., "Angiogenic activity of Onchocerca volvulus recombinant proteins similar to vespid venom antigen 5" Mol. Biochem. Parasitol. 109: 91-99 (2000). The sequences and methods of providing Ov-ASP from U.S. Pat. No. 6,723,322 (Lustigman et al.) are incorporated herein by reference.

Ov-ASP can also be obtained by isolating the protein directly from *Onchocerca volvulus* by standard methods. Some suitable methods include precipitation and liquid chromatographic protocols, such as ion exchange, hydrophobic interaction and gel filtration. (Methods Enzymol. 182 (Guide to Protein Chemistry, Deutscher, Ed. Sec. VII) 309 (1990); and Scopes, Protein Purification. Springer-Verlag, N.Y. (1987).) Ov-ASP can also be obtained by separating the protein on preparative SDS-PAGE gels, slicing out the band of interest and electroeluting the protein from the polyacrylamide matrix.

Ov-ASP can also be obtained by synthesizing the protein from individual amino acid residues, as known in the art. (Stuart and Young "Solid Phase Peptide Synthesis," $2^{nd}$ Ed., Pierce Chemical Co. (1984).)

The administration of Ov-ASP in the methods of the invention can be effected by administering the protein itself, or by introducing a nucleic acid molecule encoding the protein in a manner permitting expression of the protein. Preferably, the nucleic acid molecule is in the form of a recombinant expression vector, such as, for example, a purified plasmid. After administration of the expression vector into a mammalian cell, Ov-ASP is expressed intracellularly.

Recombinant vectors can also contain a nucleotide sequence encoding suitable regulatory elements so as to effect expression of the vector construct in a suitable host cell. Those skilled in the art will appreciate that a variety of enhancers and promoters are suitable for use in the constructs of the invention, and that the constructs will contain the necessary start, termination, and control sequences for proper transcription and processing of the nucleic acid sequence encoding an Ov-ASP when the recombinant vector construct is introduced into a subject.

Vaccine Compositions or Immunogenic Compositions Comprising Ov-ASP as an Adjuvant In one embodiment, the invention relates to vaccine compositions or immunogenic compositions comprising Ov-ASP and an antigenic moiety. Ov-ASP is used as an adjuvant in these compositions. As an adjuvant, Ov-ASP potentiates an immune response to antigens which are unrelated to Ov-ASP.

In this embodiment, vaccine compositions or immunogenic compositions which comprise at least one antigenic moiety and an effective amount of Ov-ASP are provided. The vaccines of the invention can be prophylactic vaccines or therapeutic vaccines. A prophylactic vaccine prevents a disease from occurring by priming the immune system to respond to an antigen. A therapeutic vaccine is given after infection to reduce or arrest disease progression by producing or reinforcing an immune response.

The ratio by weight of the antigenic moiety to Ov-ASP in the vaccine compositions or immunogenic compositions can be any ratio which allows for the potentiation of a specific immune response. The amount of Ov-ASP to be added to a particular antigenic moiety depends on several factors, as would be known by a skilled artisan. Factors include, for example, the age and weight of the subject mammal, the mode of administration of the composition, the inherent immunogenicity of the particular antigen, the desired form of the response (elevation of titer, prolongation of the response, or both), the presence of carriers, and other considerations that will be apparent to those skilled in the art. The amount can be determined by routine experimentation. For example, the ratio by weight of an antigenic moiety to Ov-ASP can range from about 4:1 to about 1:1, or from about 4:1 to about 1:4.

The antigenic moiety of the present invention can be an antigen or a nucleic acid molecule that encodes an antigen. An antigen is a substance to which a specific immune response in a mammal can be induced. That is, an antigen is immunogenic. A specific immune response includes a humoral and/or a cell-mediated immune response directed specifically against the antigen. For the purposes of this specification, an antigen includes substances that are capable of eliciting immune responses when administered to a mammal by itself, and substances that are capable of eliciting immune responses only when administered to a mammal together with Ov-ASP.

Antigens can, for example, be immunogenic polyamino acids. Polyamino acids include oligopeptides, polypeptides, peptides, proteins and glycoproteins. The polyamino acid can be a naturally-occurring isolated product, a synthetic product, or a genetically engineered polyamino acid.

The length of a polyamino acid is not critical as long as the polyamino acid is immunogenic when administered along with Ov-ASP. Therefore, the polyamino acid contains a sufficient number of amino acid residues to define at least one epitope of an antigen. Methods for isolating and identifying immunogenic fragments from known immunogenic proteins are described by Salfeld et al. in *J. Virol.* 63:798-808 (1989) and by Isola et al. in *J. Virol.* 63:2325-2334 (1989).

If a polyamino acid defines an epitope, but is too short to be immunogenic, it can be conjugated to a carrier molecule. Some suitable carrier molecules include keyhole limpet hemocyanin, Ig sequences, TrpE, and human or bovine serum albumin. Conjugation can be carried out by methods known in the art. One such method is to combine a cysteine residue of the fragment with a cysteine residue on the carrier molecule.

Antigens can also be a lipid, a lipopolysaccharide (glycolipid) or a polysaccharide. The length of these compounds is not critical as long as the compound induces an immune response. These compounds can also be chemically linked to protein carrier molecules in order to enhance immunogenicity. For example, a polysaccharide antigen, such as a bacterial capsular polysaccharide or fragment thereof, can be linked to a protein carrier molecule to form a glycoconjugate. Methods for preparing conjugates of bacterial capsular polysaccharide and protein carrier molecules are well known in the art, and can be found, for example, in Dick and Burret, Contrib Microbiol Immunol. 10:48-114 (Cruse J M, Lewis R E Jr., eds; Basel Kruger (1989)).

Antigens can be derived from various sources. Antigens are commercially available or can be produced as known by skilled artisans.

For example, antigens can be produced or derived from pathogenic microorganisms. Examples of microorganisms include viruses, e.g., polyoma viruses; bacteria; mycoplasmas; fungi; protozoa; and other infectious agents. An antigen can be a whole microorganism. For example, an antigen can be a modified-live (i.e., attenuated) microorganism or a killed microorganism. An antigen can also be an immunogenic component of a microorganism, or a product of a microorganism. For example, the antigen can be all or part of a protein, glycoprotein, glycolipid, polysaccharide or lipopolysaccharide which is associated with the microorganism.

Pathogenic microorganisms from which antigens can be produced or derived for vaccine purposes are well known in the field of infectious diseases. Suitable pathogenic microorganisms are listed in, for example, Medical Microbiology, Second Edition, (1990) J. C. Sherris (ed.), Elsevier Science Publishing Co., Inc., New York, and Zinsser Microbiology, 20th Edition (1992), W. K. Joklik et al. (eds.), Appleton & Lange Publishing Division of Prentice Hall, Englewood Cliffs, N.J.

Examples of microorganisms of particular interest for human vaccines include human immunodeficiency virus (HIV), coronaviruses which cause severe acute respiratory syndrome (SARS), *Chlamydia, Haemophilus influenzae, Helicobacter pylori, Moraxella catarrhalis, Neisseria gonorrhoeae, Neisseria meningitidis, Salmonella typhi, Streptococcus pneumoniae*, herpes simplex virus, a rhabdovirus, human papilloma virus, influenza, measles, respiratory syncytial virus, rotavirus, Norwalk virus, hepatitis A virus, hepatitis B virus, hepatitis C virus, tuberculosis-causing Mycobacterium, polio virus and smallpox virus.

An example of one of the preferred antigens that can be used in the pharmaceutical compositions of the present invention is a SARS-CoV polyamino acid. An example of a SARS-CoV polyamino acid is the SARS-CoV SC-1 peptide (also known as CP-1, GenBank accession number: AY274119). Another example of one of the preferred antigens is an HIV-1-CD4 polyamino acid. An example of a HIV-1-CD4 polyamino acid is the HIV-1-CD4 FLSC polypeptide. (Fouts et al, "Expression and characterization of a single-chain polypeptide analogue of the human immunodeficiency virus type 1 gp120-CD4 receptor complex" *J. Virol.* 74: 11427-11436 (2000).) An example of another preferred antigen is derived from E6 and E7 proteins of human papilloma virus (HPV), in particular from HPV-16.

Antigens for use in the present invention can also be derived from allergens. Most allergens are small proteins or protein-bound substances that are capable of producing hypersensitivity. Examples of allergens include animal dander; plants, e.g., rye grass, ragweed, timothy grass, birch trees, etc.; insect products, e.g., venom, dust mites, etc.; food; egg albumin; and various other environmental sources.

Antigens also include polyamino acids native to the mammal being treated. Such self-polyamino acids include, for example, antigens associated with tumors. Examples of such antigens include proteins derived from growth factors, growth factor receptors, and oncogene-encoded proteins. Examples of growth factor receptors include EGF receptors (HER1, HER2, HER3 and HER4), including the Neu protein associated with breast tumors, and transferrin growth factor, i.e., p97. Examples of oncogene-encoded proteins include oncofetal tumor antigens, e.g., alpha-fetoprotein and carcinoembryonic antigen. Melanoma-associated oncofetal antigens include MACE-1, MAGE-3, BAGE, GAGE-1, and GAGE-2.

Additionally, whole lysed tumor cells can be used thereby producing vaccines which comprise a collection of antigens. Examples include lysed cells from human melanoma cell lines and from human prostrate cell lines. Whole cells can be derived from the mammalian subject being treated, or can be derived from another subject.

For the purposes of this specification, the antigenic moiety also includes nucleic acid molecules which encode an antigen. The nucleic acid molecule is preferably in the form of a recombinant expression vector, such as, for example, a purified plasmid. After administration of the expression vector into a mammalian cell, the antigen is expressed intracellularly.

Recombinant vectors can also contain a nucleotide sequence encoding suitable regulatory elements so as to effect expression of the vector construct in a suitable host cell. Those skilled in the art will appreciate that a variety of enhancers and promoters are suitable for use in the constructs of the invention, and that the constructs will contain the necessary start, termination, and control sequences for proper transcription and processing of the nucleic acid sequence encoding an antigen when the recombinant vector construct is introduced into a subject.

The antigenic moiety and Ov-ASP can both be in protein form, or they can both be in nucleic acid form. If the antigenic moiety and Ov-ASP are both nucleic acids, they can both be on the same vector, or different vectors. Alternatively, the antigenic moiety can be a protein antigen and Ov-ASP can be in nucleic acid form; or the antigenic moiety can be in nucleic acid form and Ov-ASP can be a protein.

Methods of Potentiating Specific Immune Responses

The present invention includes methods of potentiating a specific immune response to an antigen in a mammal in need thereof. The methods comprise administering to the mammal an effective amount of Ov-ASP, or at least one subunit thereof; and an antigenic moiety. Ov-ASP, its subunits, and antigenic moieties suitable for use in the methods of the invention have been described above.

Ov-ASP, or its subunits; and the antigenic moieties can be co-administered separately, or as a vaccine composition or immunogenic composition, e.g., as described above.

Specific immune responses include humoral and cell-mediated responses. Humoral responses are mediated by B lymphocytes. Cell-mediated responses include the activation of T cells, including Th1, Th2 and Tc cells.

Ov-ASP can potentiate both humoral and cell-mediated responses, including Th1 and Th2 responses. Ov-ASP is particularly effective in potentiating Th1 responses, which in turn potentiate Tc responses. The potentiation of Th1 responses are particularly effective for tumor associated antigens since most of such antigens are able to induce only low frequency, low-avidity transient T-cell responses, which are biased toward Th2-type cells.

An effective amount of Ov-ASP is an amount that potentiates a specific immune response in a mammal. A potentiation of a specific immune response is an increase in the magnitude of the immune response. The minimum amount of Ov-ASP is the lowest amount which potentiates a specific immune response in the subject mammal. The maximum amount of Ov-ASP is the highest amount which does not cause undesirable or intolerable side effects in the subject mammal.

The potentiation of a humoral response can be determined by measuring the production of specific antibodies against the antigen. For example, aliquots of serum from a subject mammal can be taken and antibody titers can be assayed during the course of an immunization program. Similarly, the presence of T cells, their effector mechanisms and/or their cytokine products can be monitored. For example, the potentiation of the Th1 response can be determined by measuring the level of IFN-γ cytokines. The potentiation of the Th2 response can be determined by measuring the levels of IL-4 and IL-5 cytokines. In addition, the clinical conditions of the subject mammal can be monitored for the desired effect, e.g., an inhibition or prevention or treatment of a disease process.

The magnitude of a specific immune response is manifested by the antibody titer produced, the duration of the response, and/or the quality of the response. The magnitude of the immune response elicited by an antigenic moiety administered along with Ov-ASP is greater than the immune response elicited by the antigenic moiety administered alone.

Preventing a disease means that either the mammal does not acquire the symptoms of a disease, or that the mammal acquires fewer or less severe symptoms than the mammal would otherwise acquire without the vaccine composition. Treating a disease means that the mammal ceases to suffer from the symptoms of the disease, or that the severity of the suffering is at least partially alleviated.

Examples of infectious diseases for which the methods of the invention are effective are those diseases caused by the microorganisms listed above. Examples of diseases for which the methods of the invention are particularly effective include SARS and HIV.

Examples of tumor-associated diseases which the methods of the invention can treat and/or prevent include cancers of oral cavity and pharynx (i.e., tongue, mouth, pharynx), digestive system (e.g., esophagus, stomach, small intestine, colon, rectum, anus, liver, gallbladder, pancreas), respiratory system (e.g., larynx, lung), bones, joints, soft tissues, skin, melanoma, breast, reproductive organs (e.g., cervix, endometirum, ovary, prostate, testis), urinary system (e.g., urinary bladder, kidney, ureter, and other urinary organs), eye, brain, endocrine system (e.g., thyroid and other endocrine), lymphoma (e.g., Hodgkin's disease, non-Hodgkin's lymphoma), multiple myeloma, leukemia (e.g., acute lymphocytic leukemia, chronic lymphocytic leukemia, acute myeloid leukemia, chronic myeloid leukemia.

The vaccination or administration parameters for a particular antigen, e.g., the amount of Ov-ASP to be added to particular antigen, the dosing schedule, etc., can be determined by routine experimentation. For example, the total amount of a vaccine composition or immunogenic composition and the relative amounts of an antigen and Ov-ASP within a composition can be determined by testing the compositions in mammalian subjects. A mammalian subject can initially be given a low dose of the composition and then the dose and/or the relative amounts of the protein adjuvant and antigen can be varied while monitoring the immune response.

If inadequate vaccination or immune response is achieved then the vaccination or administration parameters can be modified in a fashion expected to potentiate the immune response, e.g., by increasing the amount of antigen and/or of Ov-ASP, by complexing the antigen with a carrier, by conjugating the antigen to an immunogenic protein, or by varying the route of administration, as is known in the art.

Methods of Stimulating a Cellular Response with Cytokine Secretion

Another embodiment of the present invention includes a method of stimulating a cellular response with cytokine secretion in a mammal in need thereof. The method comprises administering to the mammal an effective amount of Ov-ASP, or at least one subunit of Ov-ASP. Ov-ASP can be administered in the form of a pharmaceutical composition.

The cellular response is stimulated in mammals whether or not they have been previously exposed to the parasite from which Ov-ASP is derived. This unexpected discovery demonstrates that the stimulation of a cellular response by Ov-ASP is not an adaptive immune response (i.e., is not manifested by immunological memory). Instead, the cellular response is due to stimulation of the innate immune response.

An effective amount of Ov-ASP is any amount which upregulates the infection-clearing aspects of the innate immune response. The upregulation of the infection-clearing aspects of the innate immune response includes the induction of the inflammatory response, the regulation of hematopoiesis, the control of cellular proliferation and differentiation, and the healing of wounds. The minimum amount of Ov-ASP is any amount which upregulates these processes. The maximum amount of Ov-ASP is an amount which does not cause excessive proinflammatory effects.

The administration of Ov-ASP can be effected by administering the protein itself, or by introducing a nucleic acid encoding the protein in a manner permitting expression of the protein, as described above.

The particular amount of Ov-ASP administered depends upon the subject mammal being treated, the route of administration, and the pathology for which the mammal is being treated. For example, Ov-ASP could be injected into a tumor or applied to the site of a herpes virus infection to stimulate cytotoxic cellular responses that would diminish the tumor or help clear the virus infection.

Ov-ASP stimulates Th1, Th2, and regulatory Th cells via IL-10 cellular responses. However, the protein predominantly stimulates Th1 responses.

Th1 responses are especially effective for inducing antitumor responses. For example, Th2 polarized responses are elicited in patients with active cancer. Successful therapy in some cancer patients has found to be accompanied by a shift from a Th2 polarization to a Th1 polarization. Additionally, since allergens induce Th2 responses, the administration of Ov-ASP can be used to inhibit allergic responses by biasing responses to Th1.

The cytokines which are stimulated by Ov-ASP include interferon-gamma (IFN-$\gamma$), granulocyte-macrophage colony-stimulating factor (GM-CSF), tumor necrosis factor-alpha (TNF-$\alpha$), tumor growth factor-beta (TGF-$\beta$), interleukin-10 (IL-10), or combinations thereof.

Methods of Vaccinating or Generating an Immune Response against Onchocerciasis

Another embodiment of the present invention includes a method of vaccinating or generating an immune response against Onchocerciasis in a mammal. The method comprises administering to a mammal, in need thereof, an effective amount of Ov-ASP, or immunogenic fragments of Ov-ASP. Ov-ASP can be administered by itself or with an adjuvant.

Onchocerciasis, or River Blindness, occurs primarily as a result of a host inflammatory response to infection with the filarial nematode *Onchocerca volvulus*. Transmitted by the bites of blackflies from the family Simuliidae, the parasite invades the skin, subcutaneous tissues, and other tissues, producing fibrous nodules. The host inflammatory response to infection with *Onchocerca volvulus* can manifest in chronic skin disease and eye lesions.

An effective amount of Ov-ASP is an amount that prevents or inhibits Onchocerciasis. For this purpose, it is necessary for the protein to produce cytophilic antibodies. Cytophilic antibodies are antibodies that in partnership with effector cells such as neutrophils, macrophages and/or eosinophils, for example, can significantly inhibit the growth of and/or kill the parasite. Growth is significantly inhibited if the inhibition is sufficient to prevent or reduce the symptoms of the disease in an infected mammal.

The administration of Ov-ASP can be effected by administering the protein itself, or by introducing a nucleic acid encoding the protein in a manner permitting expression of the protein, as described above.

General Methods

A mammal which can benefit from the methods of the present invention can be any mammal. Categories of mammals include humans, non-human primates, livestock, domestic mammals, laboratory mammals, etc. Some examples of livestock include cows, pigs, horses, goats, cattle, etc. Some examples of domestic mammals include dogs, cats, etc. Some examples of laboratory mammals include rats, mice, rabbits, guinea pigs, etc.

A mammal in need of the methods of this invention include mammals in which the prevention or a treatment of a disease is desired. The disease can be an infectious disease; an allergy; a tumor-associated disease, such as cancer; and/or an autoimmune disease.

The pharmaceutical and vaccine compositions of the present invention can be administered by any means as long as the administration results in the desired immune response. Preferably, the compositions are administered intramuscularly, subcutaneously, transdermally, intranasally, transmucosally, intraocularly, intraperitoneally, orally or intravenously. Other suitable routes of administration include by inhalation, intratracheally, vaginally, rectally, and intraintestinally.

The means of administration of the compositions include, but not limited to, needle injection, catheter infusion, biolistic injectors, particle accelerators (i.e., "gene guns" or pneumatic "needleless" injectors—for example, Med-E-Jet (Vahlsing, H., et al., J. Immunol. Methods 171,11-22 (1994)), Pigjet (Schrijver, R., et al., Vaccine 15, 1908-1916 (1997)), Biojector (Davis, H., et al., Vaccine 12, 1503-1509 (1994)); Gramzinski, R., et al., Mol. Med. 4, 109-118 (1998)), AdvantaJet, Medijector, gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin et al., Life Sciences 65, 2193-2203 (1999)) or topical applications during surgery.

The pharmaceutical and vaccine compositions of the present invention can be formulated according to known methods. For example, the compositions can comprise a suitable carrier. Suitable carriers include any of the standard pharmaceutically acceptable carriers, such as water, phosphate buffered saline solution, and aluminum hydroxide, latex particles, bentonite, liposomes and microparticles. Suitable carriers are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995). The pharmaceutical composition can be formulated as an emulsion, gel, solution, suspension, lyophilized form, or any other form known in the art.

The vaccine compositions or immunogenic compositions of the present invention can comprise adjuvants. In the embodiment wherein Ov-ASP is used as an adjuvant, other additional adjuvants can be included. Examples of adjuvants include muramyl peptides and analogues; lymphokines, such as interferon, interleukin-1 and interleukin-6; saponins, fractions of saponins; synthesized components of saponins; pluronic polyols; trehalose dimycolate; amine containing compounds; cytokines; and lipopolysaccharide derivatives.

In addition, the vaccine and pharmaceutical composition can also contain pharmaceutically acceptable additives including, for example, diluents, binders, stabilizers, and preservatives.

The vaccine and pharmaceutical compositions can also comprise therapeutic ingredients. For example, formulations suitable for injection or infusion include aqueous and non-aqueous sterile injection solutions which may optionally contain antioxidants, buffers, bacteriostats and solutes which render the formulations isotonic with the blood of the intended recipient, and aqueous and non-aqueous sterile suspensions which can include suspending agents and thickening agents.

The vaccine and pharmaceutical compositions can be presented in unit-dose or multi-dose containers, for example, sealed ampoules and vials, and may be stored in a freeze-dried (lyophilized) condition requiring only the addition of the sterile liquid carrier, for example, water for injection, immediately prior to use.

The invention will be more fully understood in the light of the following examples. All literature and patent document citations are expressly incorporated by reference.

EXAMPLES

The Examples demonstrate that rOv-ASP-1 acts as a potent immunostimulator as well as an adjuvant. The Examples also demonstrate that rOv-ASP-1 is a potent stimulator of cytokine secretion in humans, whether or not they have been exposed to the parasite from which the protein was cloned. The adjuvant properties of rOv-ASP-1 in mice and immunostimulatory activity on human leukocytes have been shown to not be due to contaminating bacterial lipopolysaccharide (LPS), also known as endotoxin.

Example 1

Human Cytokine Responses to rOv-ASP-1.

Experiments investigating immune responses to rOv-ASP-1 in human subjects living in areas of Africa endemic for *Onchocerca volvulus* were conducted. During these studies, it was noted that the recombinant protein stimulated potent cytokine responses from control subjects who resided in the New York metropolitan area and who were never exposed to the parasite (FIG. 1). The recombinant protein stimulated significant ($P<0.05$) production of Th1-type cytokines (i.e. IFN-$\gamma$, GM-CSF and TNF-$\alpha$), and a Th2/regulatory T cell cytokine (IL-10).

Figure 2:
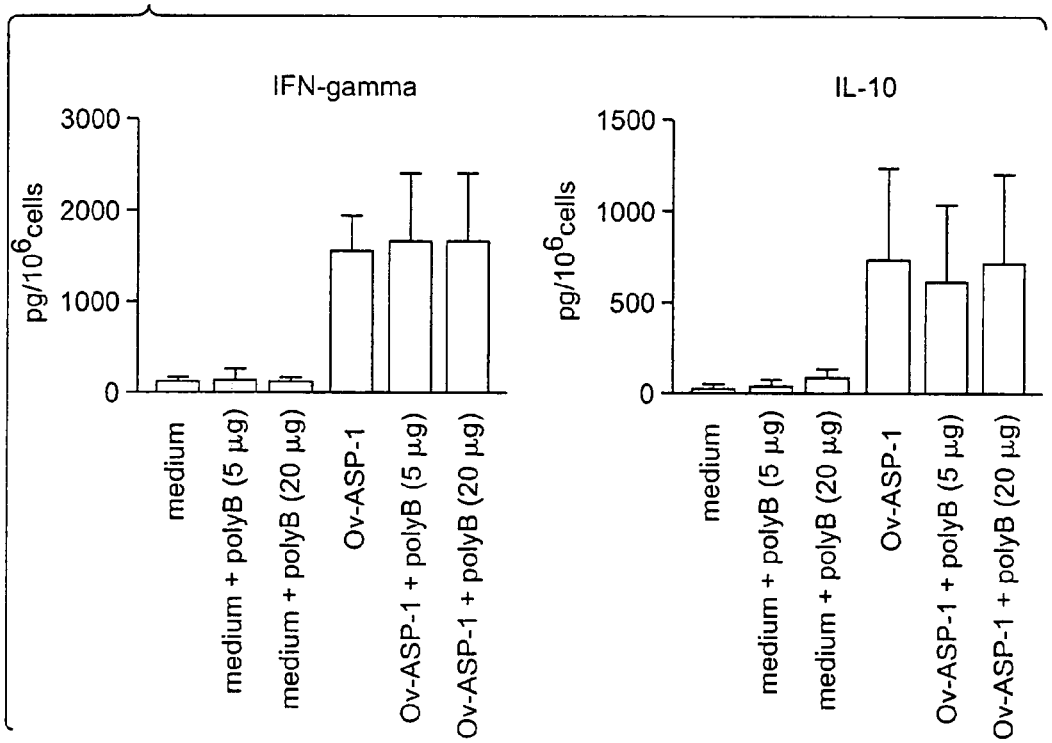
FIG. 2. Inhibition of LPS activity using polymyxin B (5 and 20 μg/mL) has no effect on the bioactivity of rOv-ASP-1 (5 μg/mL) on human PBMC (3 donors). rOv-ASP-1 was pre-incubated with polymyxin B for 1 hour at room temperature prior to adding to PBMC. Values are the mean±SD.

One concern was that residual LPS (endotoxin) derived from the bacteria *E. coli* in which rOv-ASP-1 was cloned could be contributing to the cytokine stimulating effect. Even though the optimal cytokine-inducing concentration of Ov-ASP-1 (5 μg/mL) tested negative for LPS activity in the Limulus amebocyte lysate (LAL) assay (Sigma, St. Louis, Mo.), further action was taken to ensure that the results were not due to any residual LPS in the antigen preparation. The data presented in FIG. 2 shows that the bioactivity of rOv-ASP-1 was not due to any possible LPS contamination since the cytokine production by human PBMC was not affected by the presence of polymyxin B (Sigma), an inhibitor of LPS activity.

Binding of rOv-ASP-1 to Human Peripheral Blood Mononuclear Cells.

The cells in peripheral blood mononuclear cells (PBMC) that bound the recombinant protein were identified using biotin-labeled rOv-ASP-1. As shown in Table 1, rOv-ASP-1 bound to most B cells and monocytes (>94.5%). In addition, 14.5% of CD8+ T cells and 28.7% of NK cells bound the protein. CD8+ T cells and NK cells are the likely sources of the IFN-$\gamma$ secretion induced by rOv-ASP-1.

TABLE 1

FACS analysis of binding of FITC-labeled biotinylated rOv-ASP-1 to subsets of human leukocytes in PBMC. Samples 1 and 2 were obtained from separate donors and 10,000 events were counted. Values represent the % of total cells gated for a particular CD marker that also bound FITCbiotin-rOv-ASP-1.

| Cell population | CD marker | % rOv-ASP-1 Positive cells | | |
|---|---|---|---|---|
| | | Donor # 1 | Donor # 2 | Average |
| T cells | CD4 | 3.8 | 2.3 | 3.0 |
| T cells | CD8 | 16.7 | 12.4 | 14.5 |
| B cells | CD19 | 96.1 | 93.0 | 94.5 |
| NK cells | CD56 | 30.9 | 26.5 | 28.7 |
| monocytes | CD14 | 98.6 | 97.9 | 98.3 |

Mouse Antibody and Cytokine Responses to rOv-ASP-1.

While conducting experiments designed to evaluate rOv-ASP-1 as a possible vaccine candidate against onchocerciasis in humans, BALBC/cByJ mice were vaccinated with the recombinant protein alone or with adjuvants. IgG1 and IgG2a isotypes were measured which are associated with Th2 and Th1 helper T cell responses, respectively, in mice. Broadly speaking, Th2 immune responses are active against extracellular pathogens in the tissue fluids and Th1 responses are most effective against pathogens that infect cells.

Even without adjuvants, rOv-ASP-1 was able to stimulate high titers of antibodies to itself in vaccinated mice.(Table 2). The protein stimulated both Th2 (IgG1) and Th1 (IgG2a) antibodies, with a slight Th1 dominance.

Figure 3:
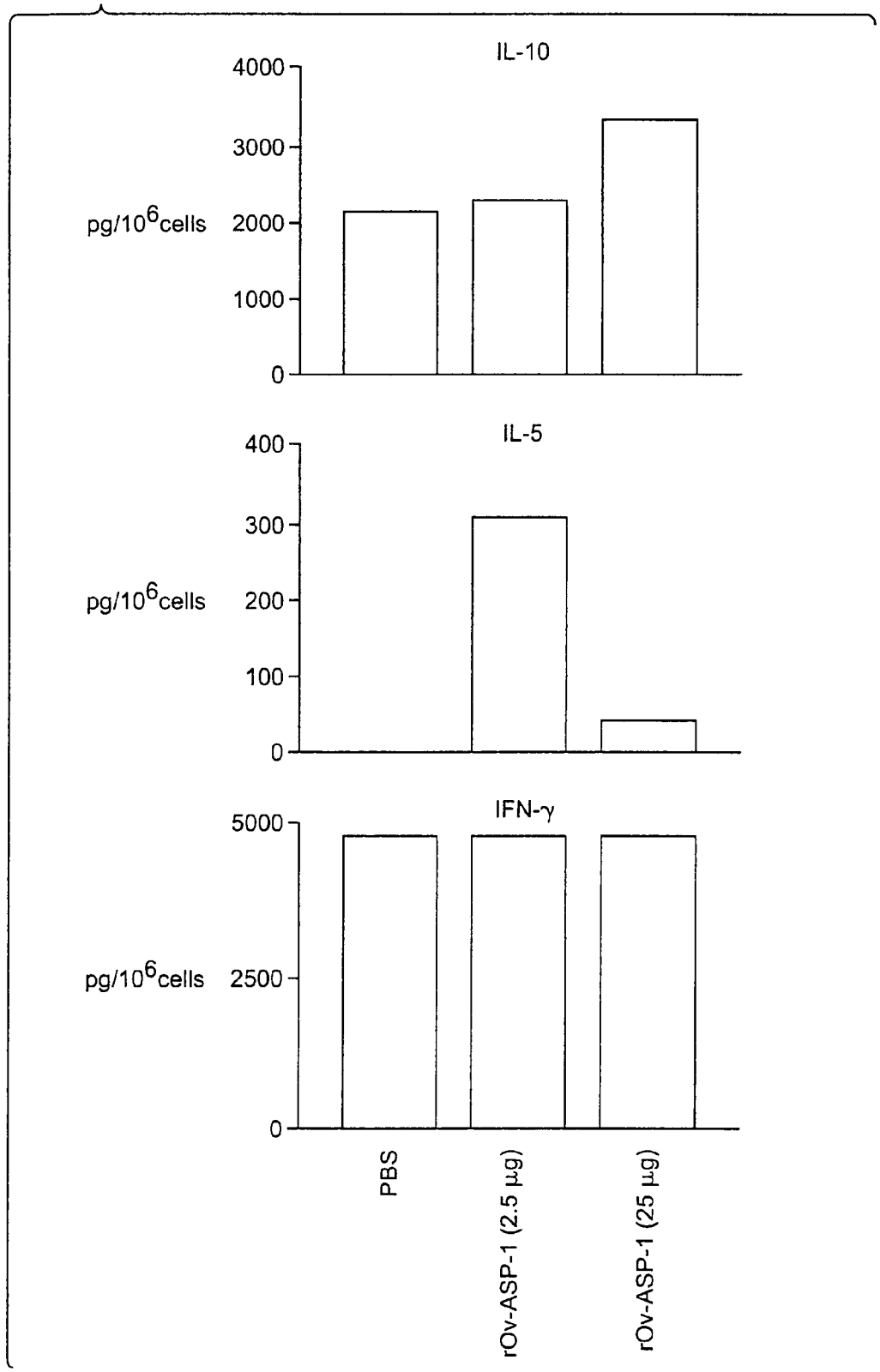
FIG. 3. Cytokines produced by spleen cells from mice immunized with PBS or rOv-ASP-1 without adjuvants and stimulated in vitro with 5 μg/mL rOv-ASP-1. Values are obtained from spleen cells pooled within each treatment group and represent the mean of triplicate cultures.

Spleen cells were collected from these mice in order to assess the cellular responses induced by rOv-ASP-1 to the protein. The spleen cells were cultured and re-stimulated in vitro with rOv-ASP-1. Interferon-gamma (IFN-γ) was measured as a marker for a Th1 response. Interleukin-5 (IL-5) was measured to indicate Th2 activity. IL-10 was measured as a Th2 and/or regulatory T cell product. The recombinant protein stimulated high levels of IFN-γ secretion from spleen cells obtained from mice injected with either PBS or rOv-ASP-1 (FIG. 3), implying direct induction of these cytokines in vitro. A similar non-antigen-specific release of IL-10 also occurred. In contrast, IL-5 was produced only by spleen cells from the mice previously exposed to rOv-ASP-1, particularly by the group that received 2.5 µg of rOv-ASP-1, indicating antigen specificity of the IL-5 response.

TABLE 2

Reciprocal end-point titers of IgG1 and IgG2a antibodies to rOv-ASP-1 in mice vaccinated with the protein in PBS or PBS alone. Titers were obtained using pooled serum samples (6 mice per group).

| | IgG1 | IgG2a |
|---|---|---|
| PBS | 0 | 0 |
| rOv-ASP-1 in PBS | 293,000 | 656,000 |

Adjuvant Studies in Mice.

Since rOv-ASP-1 was able to stimulate high-titer antibody responses to itself without added adjuvant, the question whether the protein could act as an adjuvant for antibody responses to unrelated proteins was investigated. Chicken egg albumin, also known as ovalbumin (OVA), was used as a model antigen that does not stimulate appreciable antibody responses when injected into mice without adjuvants. OVA was mixed with the commercially prepared adjuvants, alum (Sigma) or MPL+TDM (Sigma) or with the test adjuvant, rOv-ASP-1. Five groups of mice were injected subcutaneously with the commercially prepared adjuvants or, for control purposes, with OVA or with the adjuvants alone.

Each animal received 50 µg of OVA per immunization. OVA and rOv-ASP-1 were diluted in sterile, LPS- free phosphate-buffered saline (PBS).

Mice received a booster immunization after 14 days. Ten days later, serum was collected from the mice. The amounts of IgG antibodies in the serum were quantified by ELISA.

When rOv-ASP-1 was used at 25 µg/mouse, the protein (FIG. 4, black squares) surpassed the commercially prepared alum and MPL+TDM adjuvants in potency. The IgG1 anti-OVA end-point titer using rOv-ASP-1 as the adjuvant at 25 µg/mouse was 102,400. The titers obtained using MPL+TDM or alum adjuvants were 18,000 and 15,000, respectively. At the lower concentration of rOv-ASP-1 (2.5 µg), the antiOVA titer was 8,000. The IgG2a titers were considerably lower than those of IgG1 and only the rOv-ASP-1 at 25 µg induced an appreciable anti-OVA titer (25,600).

Figure 5:
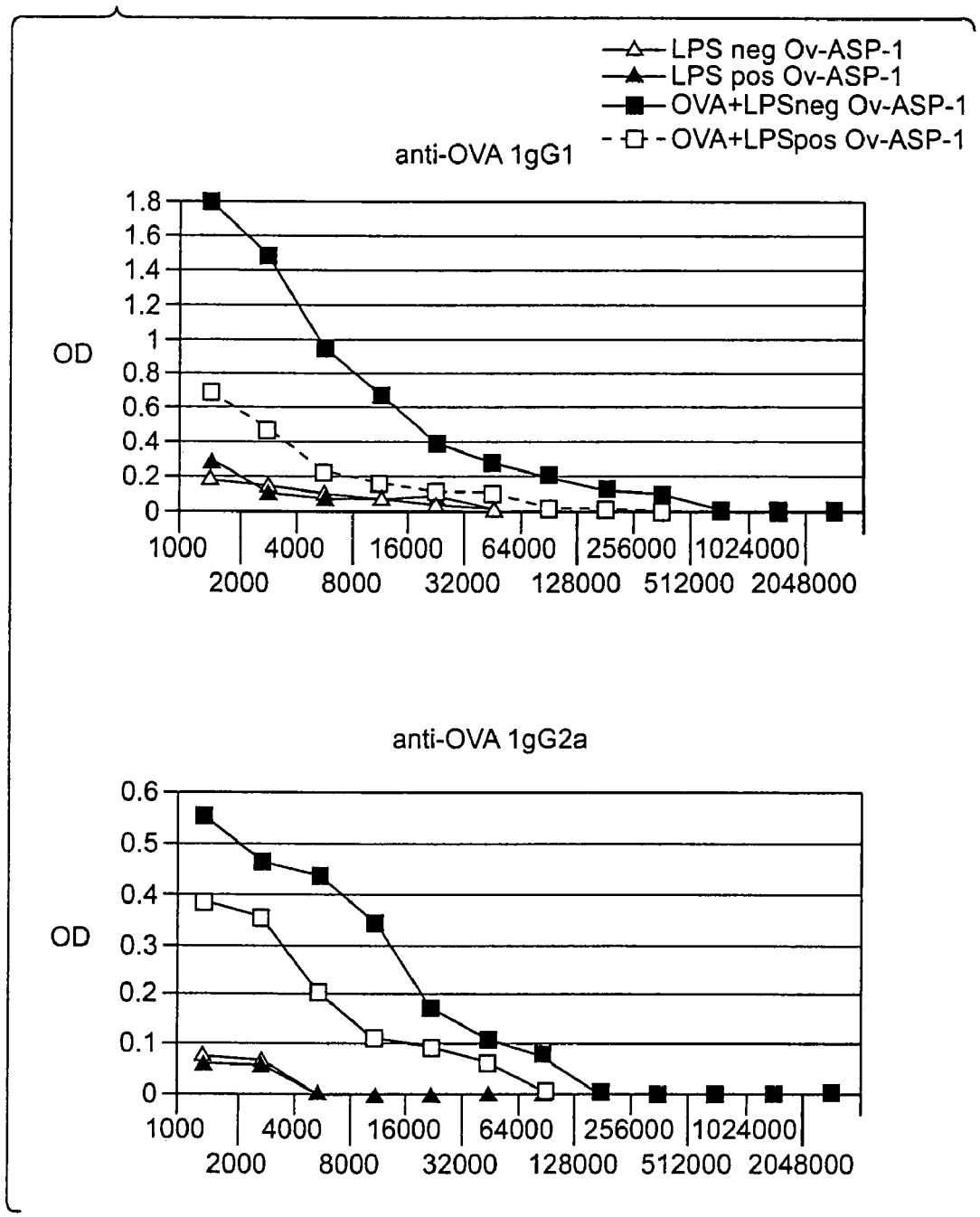
FIG. 5. Mean anti-OVA IgG1 and IgG2a titers in mice (n=5/group) bled pre-immunization (Pre) or after immunization with control treatments (PBS, OVA) or OVA combined with the test adjuvant, rOv-ASP-1 (25 μg/mouse), which was either treated (LPS−) or untreated (LPS+) with LPS-removing gel. The same symbols apply in both graphs. The end point anti-OVA IgG1 titer was 512,000 and the end point anti-OVA IgG2a titer was 128,000.

To exclude any possibility of residual LPS in rOv-ASP-1 contributing to its adjuvant effects, LPS was removed from the concentrated stock solution (2.5 mg/mL) of rOvASP-1 using a Detoxi-gel™ system (Pierce Biotechnology, Rockford, Ill.). The adjuvancy of working dilutions of LPS-free and LPS-containing batches of rOvASP-1 were compared. In FIG. 5, the open squares show that the LPS-free rOvASP-1 performed better than the same protein prepared from stock containing LPS (FIG. 5, solid circles) in augmenting antibody responses to OVA in immunized mice. The end-point antibody titer was not obtained, but the differences are clear, especially with the IgG2a isotype. Therefore, LPS as a contributing factor to the adjuvant properties of the recombinant Ov-ASP-1 protein was ruled out.

Figure 4:
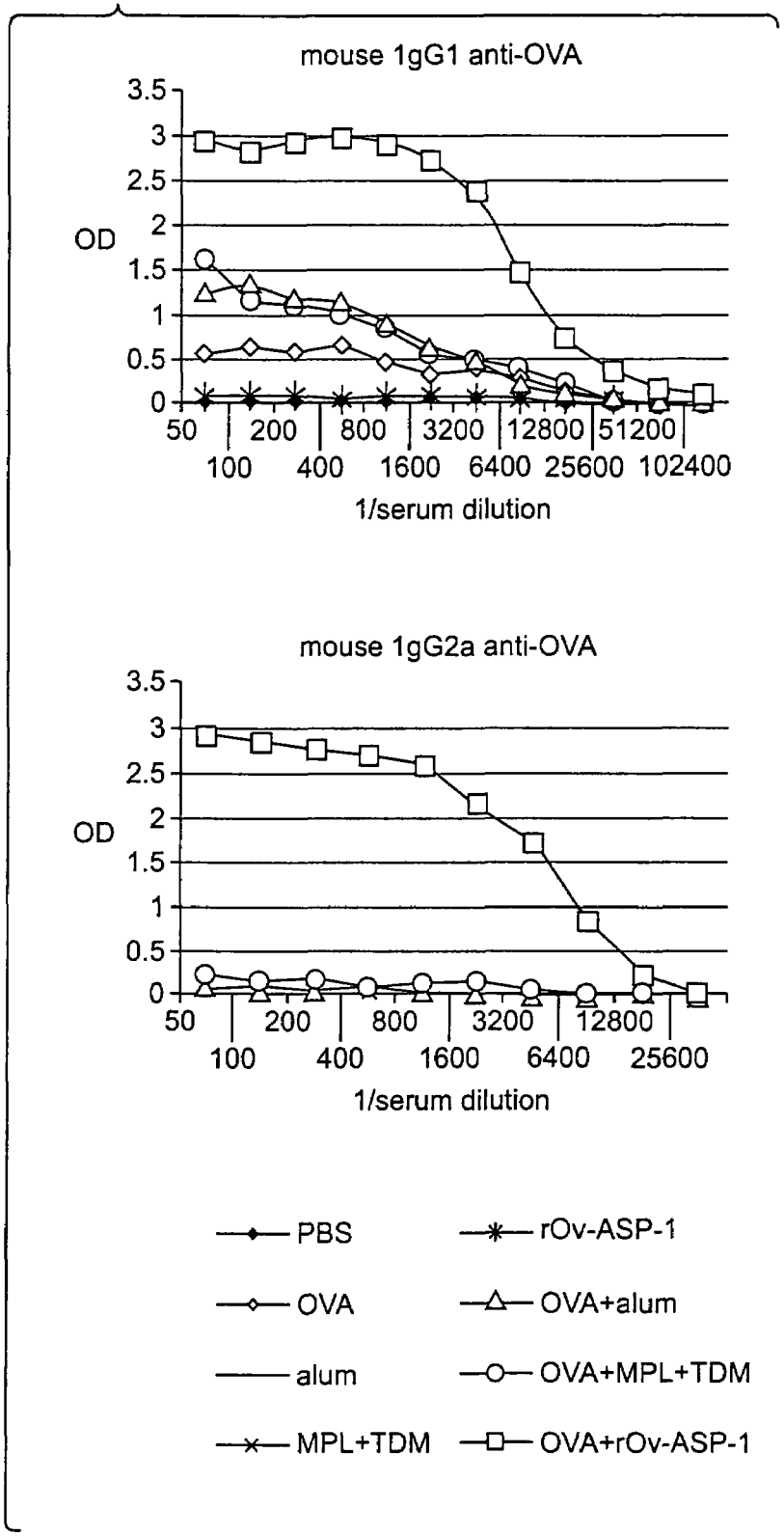
FIG. 4. Mean anti-OVA IgG1 and IgG2a in mice (n=5/group) immunized with control treatments (PBS, OVA, alum, MPL+TDM, rOv-ASP-1) or OVA combined with alum or MPL+TDM or the test adjuvant, rOv-ASP-1. Antibody amounts are expressed as optical density (OD) in the ELISA assay.
Figure 6:
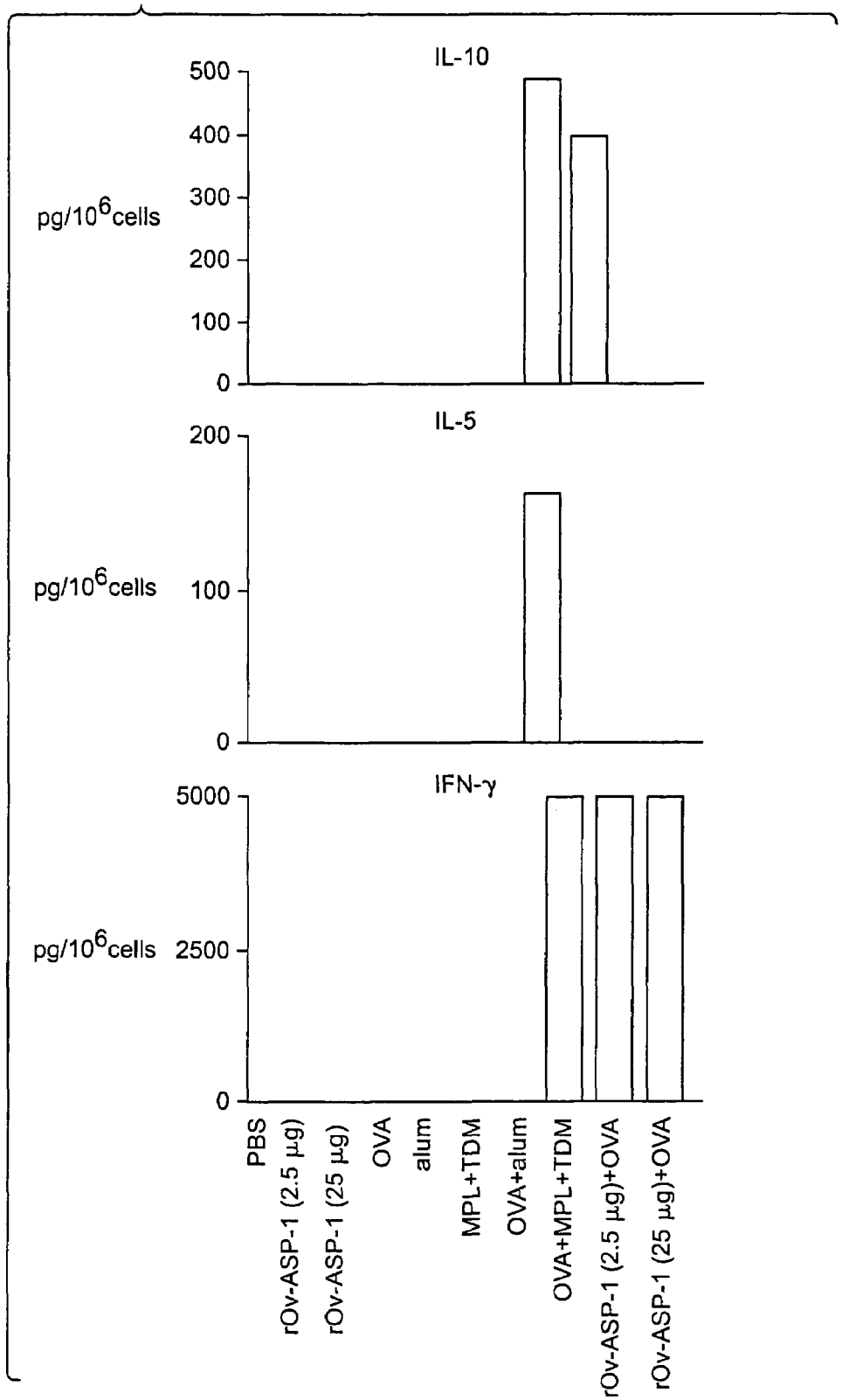
FIG. 6. Cytokines produced by spleen cells from mice immunized with OVA with or without adjuvants or relevant control treatments and re-stimulated in vitro with 5 μg/mL OVA. Values are obtained from spleen cells pooled within each treatment group and represent the mean of triplicate cultures.

Cellular responses to the immunizing antigen, OVA, were assessed by measuring cytokine secretion by spleen cells from the groups of mice depicted in FIG. 4 and these results are shown in FIG. 6.

OVA-specific IFN-γ production was seen only in mice that received the rOv-ASP-1 test adjuvant at both concentrations and also the MPL+TDM adjuvant. IL-5 was induced in response to OVA only with alum as the adjuvant and IL-10 release was stimulated only using the commercial adjuvants but not the test adjuvant. The lack of IL-5 and IL-10 suggests a predominantly Th1 bias to the rOv-ASP-1-guided antiOVA immune response.

Example 2

Evaluation of the Adjuvanticity of rOv-ASP-1 for Pathogen Antigens

The rOv-ASP-1 protein was tested to determine if the protein had similar adjuvant potency for antigens derived from human pathogens, namely SARS-CoV and HIV-1.

BALBC/cByJ mice were immunized by using the same batch of LPS-negative rOv-ASP-1 as shown in Example 1, but mixed with 50 µg of SARS-CoV CP-1 peptide (SC-1) or HIV-1-CD4 FLSC polypeptide (FLSC) instead of OVA. All immunized mice were given 2 boosts this time to optimize the response, i.e., a total of 3 injections of SC-1 or FLSC with rOv-ASP-1 as the test adjuvant or MPL+TDM as a control.

Figure 7:
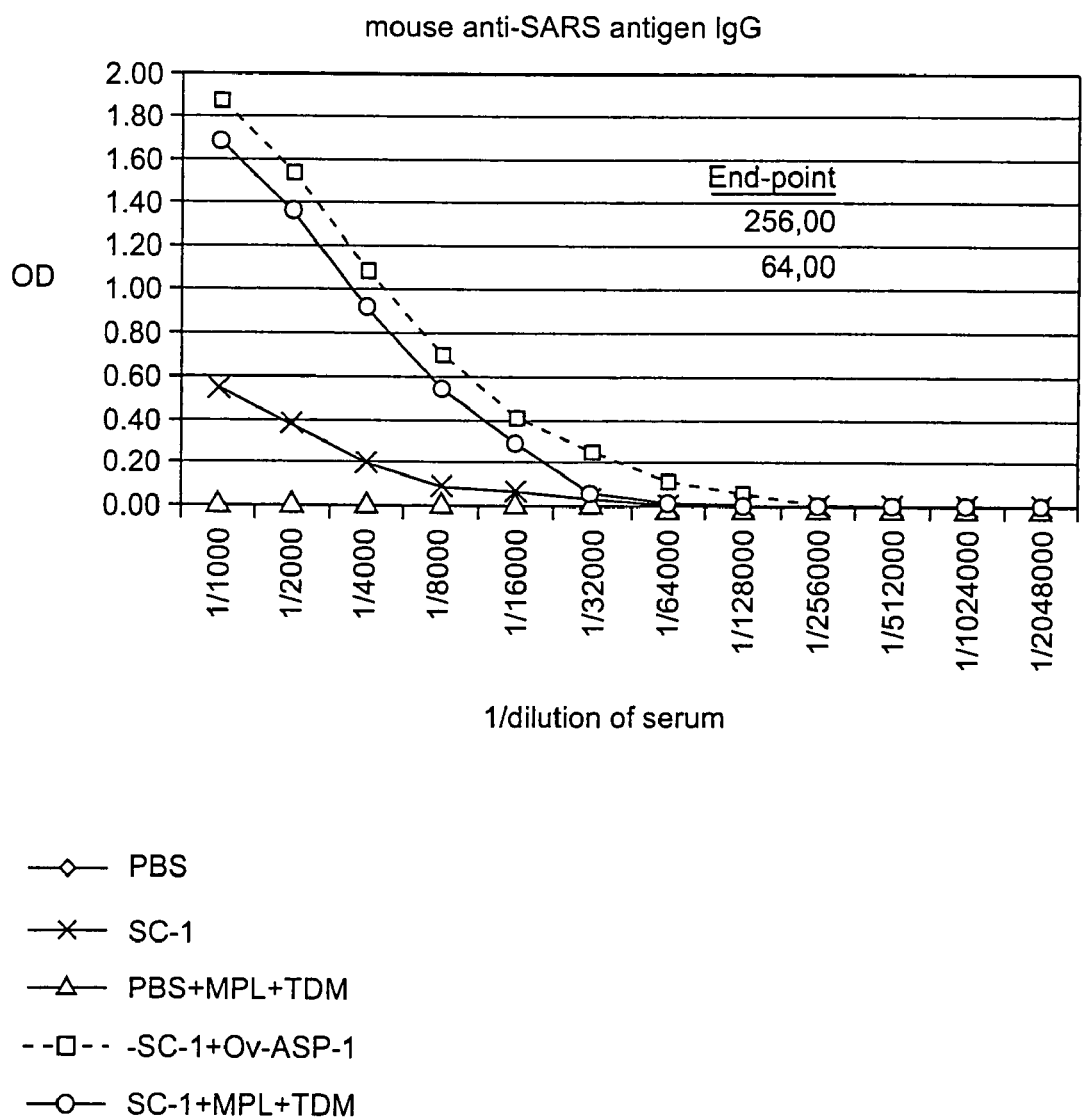
FIG. 7. Mean amounts of anti-SC-1 total IgG in mouse sera (n=5/group) after immunization with control treatments (antigens or adjuvants alone) or antigens formulated with MPL+TDM or the test rOv-ASP-1 adjuvant. Antibody amounts are expressed as optical densities (OD) in the ELISA assays. The reciprocal dilutions of serum are indicated on the x axis. T end points are denoted; 250,000 in the presence of rOv-ASP-1 and 64,000 in the presence of MPL+TDM.
Figure 8:
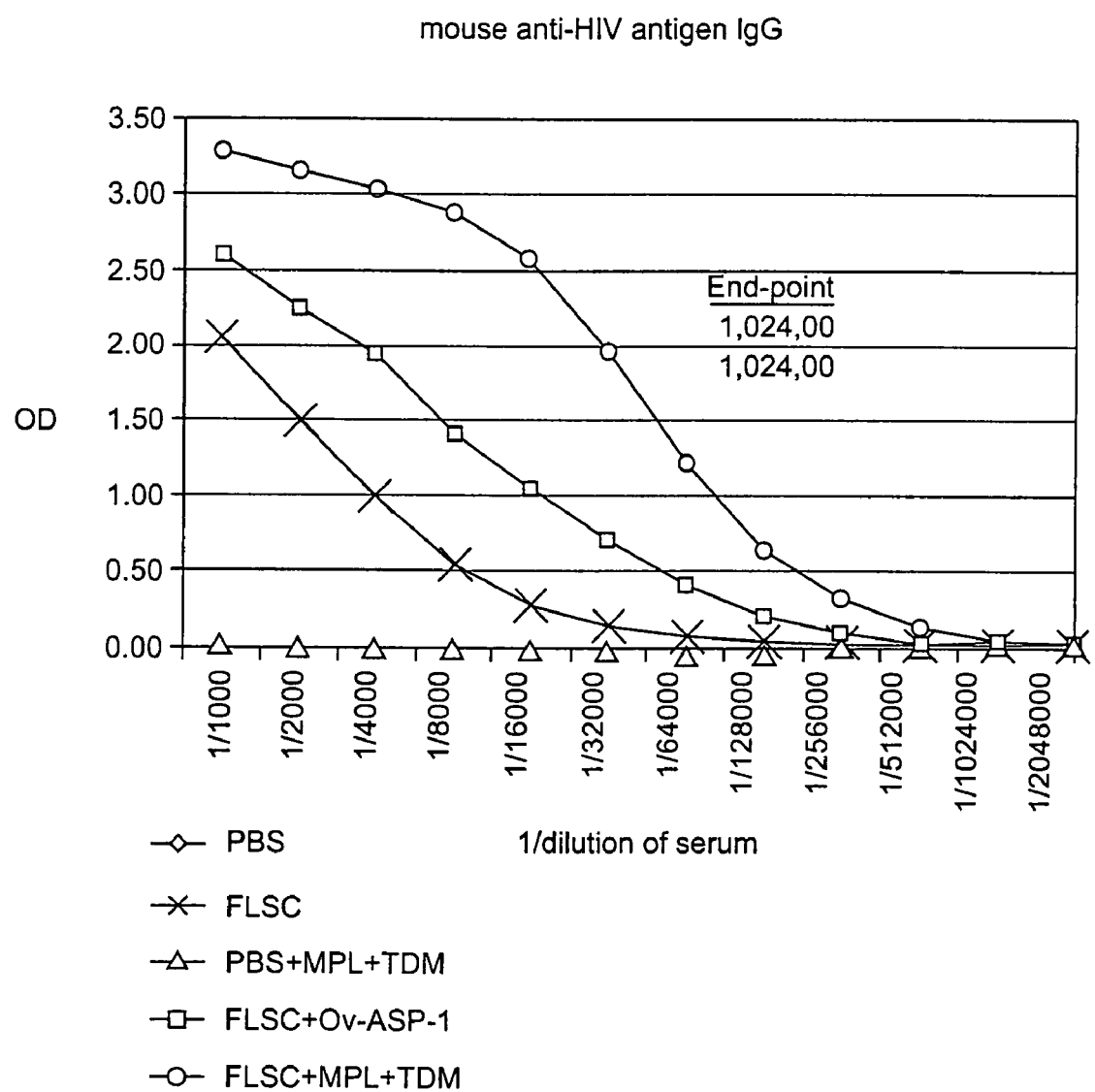
FIG. 8. Mean amounts of anti-FLSC total IgG in mouse sera (n=5/group) after immunization with control treatments (antigens or adjuvants alone) or antigens formulated with MPL+TDM or the test rOv-ASP-1 adjuvant. Antibody amounts are expressed as optical densities (OD) in the ELISA assays. The reciprocal dilutions of serum are indicated on the x axis. T end points are denoted; 1,024,000 in the presence of rOv-ASP-1 and 1,024,000 in the presence of MPL+TDM.

Using OVA as the control antigen, the end-point titers were about 2,096,000 and 1,024,000 when r-Ov-ASP-1 and MPL+TDM were used as adjuvants, respectively. These total IgG titers were approximately 10 times higher than in Example 1, suggesting that an additional boost significantly enhances antibody production. The adjuvanticity of rOv-ASP-1 for the SC-1 peptide exceeded that of MPL+TDM judging by end-point IgG titers of 256,000 vs. 64,000, respectively (FIG. 7). The anti-FLSC end-point IgG titers achieved using both adjuvants were equivalent (approximately 1,024,000; FIG. 8).

The IgG isotype responses to the SC-1 peptide and the rOv-FLSC polypeptide are summarized in Table 1. The rOv-ASP-1 protein stimulated higher IgG1, IgG2a and IgG2b titers than MPL+TDM. IgG3 titers were equally low using both adjuvants. IgG1 titers to the FLSC polypeptide were considerably lower than those to the SC-1 peptide. MPL+TDM induced a higher IgG2b titer to FLSC than rOv-ASP-1, whereas IgG1 and IgG3 titers were the same using both adjuvants.

The most striking differences between the rOv-ASP-1 and MPL+TDM -induced responses were the lack of an IgG2a (Th1) response to SC-1 using MPL+TDM, and the four-fold higher IgG2a response to FLSC adjuvanted by rOv-ASP-1 compared with MPL+TDM. In contrast to SC-1 and FLSC antigens, IgG2b and IgG3 antibodies to OVA were not detectable using either rOv-ASP-1 or MPL+TDM adjuvants (data not shown).

Each antigen model had a different behavior depending on the antigen, but the Th1 (IgG2a) response was always higher when rOv-ASP-1 was used as an adjuvant. With FLSC as the immunogen, there was a switch in IgG2a and IgG2b antibodies between ASP-1 and Ribi adjuvants. ASP-1 favored IgG2a and Ribi enhanced IgG2b. No IgE was detectable using rOv-ASP-1 as an adjuvant. IgM and IgA were not tested.

TABLE 3

Reciprocal end-point titers of mouse IgG isotypes to FLSC or CP-1 antigens formulated with either the rOv-ASP-1 test adjuvant or the MPL + TDM adjuvant. rOv-ASP-1 induced much higher IgG2a antibodies (Th1) to both antigens and biased IgG1 (Th2) to SC-1 peptide.

| | Anti-FLSC Adjuvants | | Anti-SC-1 Adjuvants | |
|---|---|---|---|---|
| IgG isotypes | rOv-ASP-1 | MPL + TDM | rOv-ASP-1 | MPL + TDM |
| IgG1 | 3,600 | 3,600 | 115,200 | 14,400 |
| IgG2a | 28,800 | 7,200 | 7,200 | 0 |
| IgG2b | 3,200 | 25,600 | 1,067 | 334 |
| IgG3 | 6,400 | 6,400 | 320 | 320 |

What is claimed is:

1. An immunogenic composition capable of inducing an immune response in a mammal against an antigen, said composition comprising an isolated antigen unrelated to *Onchocerca volvulus* activation-associated secreted protein (Ov-ASP), said antigen mixed with an adjuvant comprising an effective amount of an isolated full-length Ov-ASP comprising the amino acid sequence of SEQ ID NO: 1.

2. The composition according to claim 1, wherein the antigen is a polyamino acid.

3. The composition of claim 2, wherein the polyamino acid is an isolated SARS-CoV polyamino acid.

4. The composition of claim 3, wherein the SARS-CoV polyamino acid is the SARS-CoV SC-1 peptide.

5. The composition of claim 2, wherein the polyamino acid is an isolated HIV-1-CD4 polyamino acid.

6. The composition of claim 5, wherein the HIV-1-CD4 polyamino acid is the HIV-1-CD4-FLSC polypeptide.

7. The composition of claim 1, wherein the composition is for administration to a mammal.

8. The composition of claim 1, wherein the immune response induced against the antigen in said mammal is a humoral immune response.

9. The composition of claim 1, wherein the immune response induced against the antigen in said mammal is a cell-mediated immune response.

10. The composition of claim 9, wherein the cell-mediated immune response is a Th1 response.

11. The composition of claim 9, wherein the cell-mediated immune response is a Th2 response.

12. The composition of claim 9, wherein the cell-mediated immune response is a Th1 and a Th2 response.

13. The composition of claim 1, wherein the antigen to the Ov-ASP ratio by weight is from 4:1 to 1:1.

14. The composition of claim 1, wherein the antigen to the Ov-ASP ratio by weight is from 4:1 to 1:4.

15. The method of potentiating a specific immune response to an antigen in a mammal in need thereof, the method comprising administering to the mammal the immunogenic composition of any one of claims 1-14.

* * * * *

UNITED STATES PATENT AND TRADEMARK OFFICE
CERTIFICATE OF CORRECTION

| | | |
|---|---|---|
| PATENT NO. | : 7,700,120 B2 | Page 1 of 1 |
| APPLICATION NO. | : 11/153222 | |
| DATED | : April 20, 2010 | |
| INVENTOR(S) | : Angus J. MacDonald and Sara Lustigman | |

It is certified that error appears in the above-identified patent and that said Letters Patent is hereby corrected as shown below:

Column 1, line 8, add the following:

STATEMENT REGARDING FEDERALLY SPONSORED RESEARCH

This invention was made with Government support under Grant No. AI42328-04 from the National Institutes of Health. The Government may have certain rights in this invention.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,700,120 B2  
APPLICATION NO. : 11/153222  
DATED : April 20, 2010  
INVENTOR(S) : Angus J. MacDonald and Sara Lustigman It is certified that error appears in the above-identified patent and that said Letters Patent is hereby corrected as shown below:

Column 1, line 8, "STATEMENT REGARDING FEDERALLY SPONSORED RESEARCH
This invention was made with Government support under Grant No. AI42328-04 from the National Institutes of Health. The Government may have certain rights in this invention." should be changed to --STATEMENT REGARDING FEDERALLY SPONSORED RESEARCH
This invention was made with Government support under Grant No. AI42328-04 from the National Institutes of Health. The Government has certain rights in the invention.--

Signed and Sealed this  
Tenth Day of May, 2011

David J. Kappos  
*Director of the United States Patent and Trademark Office*

SEQUENCE LISTING

```
<160> NUMBER OF SEQ ID NOS: 3

<210> SEQ ID NO 1
<211> LENGTH: 223
<212> TYPE: PRT
<213> ORGANISM: Onchocerca volvulus

<400> SEQUENCE: 1

Met Ile Leu Phe Ile Ile Phe Pro Ala Ile Val Val Ala Val Thr Gly
1               5                   10                  15

Tyr Asn Cys Pro Gly Gly Lys Leu Thr Ala Leu Glu Arg Lys Lys Ile
            20                  25                  30

Val Gly Gln Asn Asn Lys Tyr Arg Ser Asp Leu Ile Asn Gly Lys Leu
        35                  40                  45

Lys Asn Arg Asn Gly Thr Tyr Met Pro Arg Gly Lys Asn Met Leu Glu
    50                  55                  60

Leu Arg Trp Asp Cys Lys Leu Glu Ser Ser Ala Gln Arg Trp Ala Asn
65                  70                  75                  80

Gln Cys Ile Phe Gly His Ser Pro Arg Gln Gln Arg Glu Gly Val Gly
                85                  90                  95

Glu Asn Val Tyr Ala Tyr Trp Ser Ser Val Ser Val Glu Gly Leu Lys
            100                 105                 110

Lys Thr Ala Gly Thr Asp Ala Gly Lys Ser Trp Trp Ser Glu Leu Pro
        115                 120                 125

Lys Leu Tyr Glu Asn Asn Pro Ser Asn Asn Met Thr Trp Lys Val Ala
    130                 135                 140

Gly Gln Gly Val Leu His Phe Thr Gln Met Ala Trp Gly Lys Thr Tyr
145                 150                 155                 160

Lys Ile Gly Cys Gly Val Ala Thr Gln Cys Asp Gly Gly Arg Thr Leu
                165                 170                 175

Ile Val Ile Cys His Tyr Ser Pro Gly Gly Asn Met Gly Glu Val
            180                 185                 190

Ile Tyr Gln Arg Gly Asn Pro Cys Asn Pro Cys Lys Val Asp Lys Asp
        195                 200                 205
```

-continued

```
Cys Tyr Thr Lys Lys Cys Leu Ser Lys Ser Gly Leu Cys Arg Lys
    210                 215                 220

<210> SEQ ID NO 2
<211> LENGTH: 253
<212> TYPE: PRT
<213> ORGANISM: Onchocerca volvulus

<400> SEQUENCE: 2

Met Ile Leu Phe Leu Ile Phe Pro Ala Ile Ile Val Ala Val Thr Gly
1               5                   10                  15

Tyr Asp Cys Tyr Arg Gly Lys Leu Thr Pro Gln Tyr Arg Glu Lys Ile
            20                  25                  30

Val Arg Glu His Asn Arg Leu Arg Ser Lys Leu Ala Lys Gly Thr Tyr
        35                  40                  45

Lys Asn Ser Ala Gly Lys Trp Met Pro Lys Gly Lys Asn Met Met Glu
    50                  55                  60

Met Lys Trp Asp Cys Glu Leu Glu Leu Met Ala Gln Arg Trp Ala Asp
65                  70                  75                  80

Gln Cys Val Ser Gly Asn Ser Pro Lys Asp Arg Arg Gly Arg Ile Gly
                85                  90                  95

Glu Asn Val Tyr Thr Gln Arg Ser Asp Thr Ser Val Ala Val Tyr Gly
            100                 105                 110

Thr Ser Gly Ile Met Ile Ala Leu Glu Ser Trp Trp Val Glu Leu Thr
        115                 120                 125

Arg Ser Tyr Lys Asn Asn Pro Ser Asn Lys Tyr Thr Ser Ile Val Ala
    130                 135                 140

Asn Arg Gly Val Ser Asn Phe Thr Gln Leu Ala Trp Gly Lys Thr Tyr
145                 150                 155                 160

Lys Val Gly Cys Gly Ile Ala Thr His Cys Asp Gly Gly Lys Ala Phe
                165                 170                 175

Val Ala Val Cys Gln Tyr Asn Pro Gly Gly Asn Thr Met Gly Glu Ser
            180                 185                 190

Ile Tyr Glu Lys Gly Arg Pro Cys Lys Thr Asp Arg Asp Cys Ser Ser
        195                 200                 205

Arg Lys Cys Cys Lys Arg Ile Trp Ile Val Gln Ile Glu Phe Leu His
    210                 215                 220

Leu Ile Phe Gly Phe Ala Met His Pro Tyr Ile Tyr Phe Ser Ala Lys
225                 230                 235                 240

Lys Leu Lys Lys Ile Phe Ile Ile Lys Tyr Glu Tyr Ile
                245                 250

<210> SEQ ID NO 3
<211> LENGTH: 220
<212> TYPE: PRT
<213> ORGANISM: Onchocerca volvulus

<400> SEQUENCE: 3

Met Ile Leu Phe Ile Ile Phe Pro Ala Ile Ile Val Ala Val Thr Gly
1               5                   10                  15

His Asp Cys His Arg Gly Lys Leu Thr Ser Leu Gln Arg Asp Ile Ile
            20                  25                  30

Tyr Asp Glu His Asn Lys Tyr Arg Ser Arg Leu Val Lys Gly Asn Phe
        35                  40                  45

Ala Asn Lys Asp Gly Asn Ser Met Pro Lys Gly Lys Asn Met Met Glu
    50                  55                  60
```

```
-continued

Met Glu Trp Asp Cys Glu Leu Glu Ile Ser Ala Gln Asn Trp Ala Asp
 65              70                  75                  80

Gln Cys Ile Phe Gly Tyr Ser Pro Glu Asn Gln Arg Glu Gly Val Gly
                 85                  90                  95

Glu Asn Ile Tyr Ala Leu Gly Leu Pro Lys Asp Val Glu Val Phe Asn
                100                 105                 110

Thr Ser Ala Ala Leu Phe Ala Ile Glu Ser Trp Trp Thr Glu Leu Ile
            115                 120                 125

Arg Ser Tyr Arg Asn Asn Pro Ser Asn Lys Leu Thr Ser Ser Val Ala
            130                 135                 140

Ser Gln Asp Val Leu His Phe Thr Gln Met Ala Trp Gly Lys Thr His
145                 150                 155                 160

Lys Val Gly Cys Gly Ile Ala Met His Cys Asp Asp Gly Glu Ala Phe
                165                 170                 175

Ile Val Val Cys His Tyr Ala Pro Arg Gly Asn Thr Ile Gly Glu Leu
                180                 185                 190

Ile Tyr Glu Gln Gly Ser Pro Cys Lys Val Asn Lys His Cys Arg Thr
            195                 200                 205

Lys Lys Cys Ser Arg Lys Ser Gly Leu Cys Lys Lys
            210                 215                 220
```